United States Patent [19]

Wolf et al.

[11] 4,048,221

[45] Sept. 13, 1977

[54] DIOLS CONTAINING SULPHONIC ACID GROUPS BASED ON DIHYDROXY ALKENES

[75] Inventors: Gerhard Dieter Wolf, Dormagen; Francis Bentz, Cologne; Gunther Nischk, Dormagen, all of Germany

[73] Assignee: Bayer Aktiengesellschaft, Leverkusen, Germany

[21] Appl. No.: 555,228

[22] Filed: Mar. 4, 1975

[30] Foreign Application Priority Data

Mar. 7, 1974 Germany .............................. 2410862

[51] Int. Cl.$^2$ ................. C07C 143/42; C07C 143/10; C08G 63/12
[52] U.S. Cl. ........................... 260/512 C; 260/513 R; 260/513 B; 260/75 S; 260/77.5 AP; 260/DIG. 19; 526/30
[58] Field of Search ........... 260/513 R, 513 B, 513 T, 260/512 R, 512 C

[56] References Cited

U.S. PATENT DOCUMENTS

| 2,602,054 | 7/1952 | Groote | 260/513 B |
| 3,002,903 | 10/1961 | Foulke et al. | 260/513 R |
| 3,041,256 | 6/1962 | Kleiner et al. | 260/513 B |
| 3,255,239 | 6/1966 | Gardenier | 260/513 B |
| 3,418,239 | 12/1968 | Cooper | 260/512 R |
| 3,860,638 | 1/1975 | Beach et al. | 260/513 B |

*Primary Examiner*—James O. Thomas, Jr.
*Assistant Examiner*—Nicky Chan
*Attorney, Agent, or Firm*—Gene Harsh; Joseph C. Gil; William E. Parry

[57] ABSTRACT

The instant invention relates to sulphonates containing ether groups and derived from dihydroxy alkane sulphonic acids, and to a process for their production. They are obtained by the addition of bisulphites to (poly)alkoxylated dihydroxy alkenes.

2 Claims, No Drawings

DIOLS CONTAINING SULPHONIC ACID GROUPS BASED ON DIHYDROXY ALKENES

BACKGROUND OF THE INVENTION

It is known that alkali metal hydrogen sulphites can be added to double bonds activated by electron-attracting groups, for example nitrile or ester groups (cf. R. T. E. Schenck and J. Danishefsky, J. Org. Chem. 16, 1683 (1951); O. Bayer, Ang. Chem. 61, 233 (1949)). It is also known that bisulphites can be added to aliphatic double bonds which are only weakly activated. It is described, for example, in the literature that bisulphites can be added to allyl alcohol (see M. S. Kharasch, E. M. May and F. R. Mayo, J. Org. Chem. 3, 175 (1939)). This reaction produced 3-hydroxy propane sulphonic acid in the form of its salts in a yield of only 30%. The yield from the reaction of allyl alcohol and bisulphites was increased (German Pat. No. 915,693), but it was not possible to completely suppress the formation of secondary products which are assumed to be compounds of the following structure:

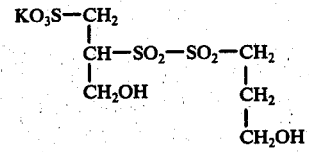

Additionally, complete separation of the inorganic salts formed during the reaction from the sulphonate is difficult.

Salts of 3-hydroxy-2-hydroxy methyl propane sulphonic acid are also known and can be obtained by reacting 2-methylene-1,3-propane diol with bisulphites (DOS No. 2,224,304). However, 2-methylene-1,3-propane diol can only be obtained at high cost and in small quantities, so that the 3-hydroxy-2-hydroxy methyl-1-propane sulphonic acid obtained therefrom cannot be used on a wide scale. In addition, it is relatively difficult to separate this 3-hydroxy-2-hydroxy methyl propane sulphonic acid from the organic salts formed during the reaction. This also applies to the production of 1,4-dihydroxy-2-butane sulphonic acid which may be used for the preparation of stable baths used for copper plating in the absence of an electrical current (DOS No. 2,132,003).

Accordingly, there is a need for diols containing sulphonate groups which can be produced easily and inexpensively and which, in addition, can be used for a variety of applications by virtue of their favorable properties.

DESCRIPTION OF THE INVENTION

It has now surprisingly been found that bisulphites can be added to alkoxylated dihydroxy alkenes in high yields and purity.

Accordingly, the invention relates to dihydroxy sulphonates containing ether groups and corresponding to the following general formula

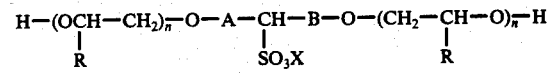

in which
A and B, which may be the same or different, represent straight-chain or branched alkylene radicals with 1 to 6 carbon atoms, the total number of carbon atoms in A and B being from 3 to 7,
R represents hydrogen, $C_1$–$C_4$-alkyl or phenyl,
X represents $NH_4$ or an alkali metal and
n is a number from 1 to 30, preferably a number from 1 to 10.

The invention also relates to a process for the production of these compounds, which is distinguished by the fact that the dihydroxy alkenes are (poly)-alkoxylated and the resulting alkoxylated derivatives, which correspond to the general formula

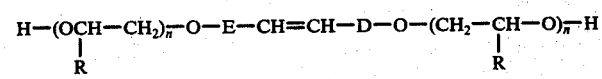

in which
E and D, which may be the same or different, represent linear or branched alkylene radicals with 1 to 5 carbon atoms, the total number of carbon atoms in E and D not exceeding 6, and
R represents hydrogen, $C_1$–$C_4$-alkyl or phenyl,
n is an integer from 1 to 30, preferably from 1 to 10,
are reacted with bisulphites corresponding to the general formula
X—$HSO_3$
in which
X represents $NH_4$ or an alkali metal,
in aqueous medium, in the presence of catalytically active oxygen, at temperatures of up to 100° C and at pH-values in the range from 3 to 9 preferably in the range from 7 to 8, the molar ratio of bisulphite to diol being from 1:1 to 5:1.

These dihydroxy sulphonates containing ether groups can be obtained in very pure form and in very good yields in the manner described above. Separation of the inorganic salts formed during the reaction is surprisingly easy and is carried out by extracting the sulphonates with acetone, acetone/water mixtures, chlorinated hydrocarbons, alcohols or alcohol/water mixtures. After extraction, the sulphonates do not contain any salts (even minute quantities could not be detected).

In addition to this easy and quantitative separation of the inorganic salts, another advantage which should be mentioned is the wide scope of application of the compounds according to the invention. They are eminently suitable for use as comonomers for the production of acid-modified polyesters and polyurethanes and, after they have been reacted for example with chloroacetic acid (esters), are useful for the production of acid-modified polyamides. The derivatives which are more highly ethoxylated and/or propoxylated, optionally after reaction with isocyanates for example to form diurethanes, are excellent antistatic agents and are used as additives in the production of antistatically finished films, sheets and filaments of polyacrylonitrile or polyamide.

The unsaturated diols used as starting materials are produced by alkoxylating an alkene, such as, 1-butene-3,4-diol, 2-methylene-1,3-propane diol, 3-hexene-2,5- diol and the like. The presently preferred alkene is 2-butene-1,4-diol. The diols are then alkoxylated with ethylene oxide, propylene oxide, butylene oxide, styrene oxide or the like. This reaction is carried out in the absence or presence of solvents, such as dioxane or DMF, and in the presence of small quantities, preferably 0.2 to 2% by weight, of a basic catalyst, such as NaOH, KOH, sodium or potassium methylate, at temperatures in the range from 50° to 180° C, preferably at temperatures in the range from 100° to 160° C, and optionally under pressure in an autoclave. Substances ranging from highly viscous to wax-like are formed and may be characterized by their degree of alkoxylation by determining the OH-number or by NMR-spectroscopy.

Sulphonation may be carried out with commercial-grade bisulphite liquors or with bisulphite liquors freshly prepared by the introduction of SO$_2$ into the corresponding aqueous ammonium or alkali metal hydroxide solution. The bisulphites usable are known in the art.

The addition reaction may be carried out at temperatures of up to 100° C, preferably from −10° C to 70° C, and most preferably at room temperature, by introducing the unsaturated diols or their aqueous solutions into or slowly adding them dropwise to the bisulphite liquor. The molar ratio of bisulphite to diol should be from 1:1 to 5:1, preferably from 1.1:1 to 2:1. Catalysts suitable for the reaction include air, oxygen or oxygen from oxygen-yielding compounds, for example, H$_2$O$_2$, the oxygen having to be present in the reaction mixture in as fine a state of dispersion as possible, which state can readily be obtained by means of suitable stirrers. A high yield of sulphonate depends upon the pH-value of the reaction solution which should be between a pH 3 and a pH 9, pH-values in the range from 5 to 8 being preferred and a pH-value of around 7 being particularly preferred. The required pH-value is adjusted by adding the necessary quantity of ammonia or alkali liquor, for example, to the bisulphite solution. During the reaction, the pH-value increases. However, the pH-value is kept at the required value by simultaneously adding dilute acid or by introducing more sulphur dioxide. The reaction is complete when there is no further change in the pH-value. Heat is given off during the reaction, and, if desired, the reaction mixture may be cooled.

In cases where unsaturated diols having a relatively high degree of alkoxylation are reacted, it is advisable to initially introduce the unsaturated diol into the reactor followed by dropwise addition of the solution of the bisulphite, but again under the reaction conditions described above.

Separation of most of the inorganic salts is preferably carried out by concentrating the solution to approximately half its volume and filtering the crystals precipitated. The required reaction products can be separated off from the residual inorganic salts by extraction with acetone, acetone/water mixtures, chlorinated hydrocarbons, alcohols and with alcohol/water mixtures. The sulphonates accumulate in analytically pure form in yields of up to 90%.

The sulphonates containing ether groups produced in accordance with the invention are eminently suitable for use as comonomers for the production of acid-modified polyesters and polyurethanes and, after they have been reacted for example with chloroacetic acid (esters), also for the production of acid-modified polyamides. In addition, the derivatives which are more highly ethoxylated and/or propoxylated, optionally after reaction with isocyanates to form diurethanes, are excellent antistatic agents and are used as additives in the production of polyacrylonitrile or polyamide films, sheets and filaments with antistatic properties.

The production of a copolyester for polyester fibers which may be dyed with basic dyes is described in the following:

194.0 parts by weight of terephthalic acid dimethyl ester, 186.0 parts by weight of ethylene glycol and 14.4 parts by weight of a dihydroxy sulphonate corresponding to the formula $$H-(OCH_2-CH_2)_{1.9}-OCH_2-\underset{SO_3Na}{\underset{|}{CH}}-CH_2-CH_2-O-(CH_2CH_2O)_{1.9}-H$$

in admixture with 0.5 parts by weight of zinc acetate and 0.6 parts by weight of antimony trioxide, are introduced into a reaction vessel equipped with an anchor agitator, gas inlet pipe, dephlegmator, condenser, vacuum tube and receiver. The contents of the reaction vessel are heating to 165° C while nitrogen is passed over, followed by transesterification for 2 hours. The temperature is then increased to 280° C over a period of 2 hours. After the supply of nitrogen has been shut off, the pressure is gradually reduced over a period of one hour to 0.03 Torr. The speed of the stirrer then has to be reduced from approximately 150 to approximately 20 revolutions per minute because of the steady increase in the viscosity of the melt. Polycondensation is complete after another 3.5 hours. The colorless, homogeneous highly viscous melt can be processed into shaped articles, especially filaments. The stretched filaments can be dyed dark blue with a basic dye. The dye finish is washproof.

The polyester has a softening point of 250 to 263° C and a relative solution viscosity $\eta_{rel}$ of 1.96 (as measured on a solution of 1 g of substance in 100 ml of m-cresol at a temperature of 25° C).

EXAMPLE 1

Ethoxylated 1,4-dihydroxy-2-butene
H—(OCH$_2$—CH$_2$)$_{1.9}$—O—CH$_2$—CH=CH—CH$_2$—O—(CH$_2$—CH$_2$—O)$_{1.9}$—H 445 g (5 mols) of 1,4-dihydroxy-2-butene were reacted with 880 g (20 mols) of ethylene oxide in an autoclave at 90° to 110° C following the addition of 4.5 g of sodium as catalyst. The ethylene oxide was added in such a way that an internal pressure of at most 3 atms was maintained throughout the reaction. After the ethylene oxide has been added, the reaction mixture was stirred until the excess pressure had disappeared.

Determination of the content of OH-groups produced a figure of 13.29 OH %, corresponding to a molecular weight of 225 and to a total ethylene oxide content of 2 $n = 3.8$.

EXAMPLE 2

Propoxylated 1,4-dihydroxy-2-butene

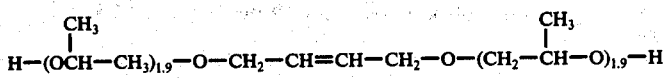

As in Example 1, 445 g (5 mols) of 1,4-dihydroxy-2-butene were reacted with 1160 g (20 mols) of propylene oxide in an autoclave at 140° to 150° C in the presence of 1% of sodium as catalyst. Determination of the content of OH groups produced a figure of 10.97 OH %, corresponding to a molecular weight of 310 and to a total propylene oxide content of $2n = 3.8$.

EXAMPLE 3

Ethoxylated butane diol sulphonate

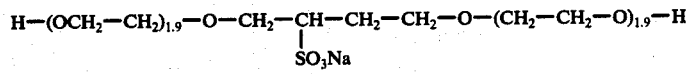

510 g (2 mols) of ethoxylated 1,4-dihydroxy-2-butene (prepared in accordance with Example 1) were dissolved in 1.5 liters of water, followed by the addition of 520 g (2 mols) of 40% sodium bisulphite solution adjusted to pH 7.1 with dilute sodium hydroxide. The required reaction was initiated by blowig in air through a glass frit, producing an increase in temperature to 35° - 38° C and a rise in the pH-value.

The pH-value was kept at 7 to 7.1 by the simultaneous dropwise addition of dilute $H_2SO_4$. The reaction was complete when the pH-value remained constant. The aqueous neutral solution was concentrated to dryness and the sulphonate extracted with methanol. Yield: 586 g (81.5 % of the theoretical).

EXAMPLE 4

Ethoxylated butane diol sulphonate

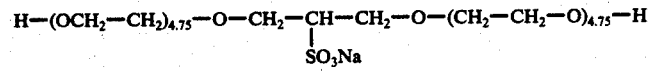

As in Example 3, 253 g (0.5 mol) of ethoxylated 1,4-dihydroxy-2-butene (total degree of ethoxylation $2n = 9.5$) and 130 g (0.5 mol) of 40% sodium bisulphite solution were reacted in 1.5 liters of water by blowing in air at a constant pH-value of 7.0 to 7.1. After sulphonation, the required compound was isolated by concentrating the aqueous solution to dryness, followed by extraction with methylene chloride.

Yield: 262 g (86.1% of the theoretical).

EXAMPLE 5

Propoxylated butane diol sulphonate

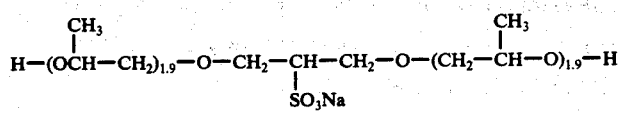

620 g (2 mol) of propoxylated 1,4-dihydroxy-2-butene (prepared in accordance with Example 2) were dissolved in 1.5 liters of water. 520 g (2 mols) of 40% sodium bisulphite solution were then added dropwise in the presence of air finely dispersed in the reaction medium. The pH-value was kept constant at 7 to 7.1 by the dropwise addition of dilute sulphuric acid. After the aqueous solution had been concentrated to dryness, the required compound was extracted with methylene chloride.

Yield: 662 g (80.1 % of the theoretical).

EXAMPLE 6

Propoxylated butane diol sulphonate

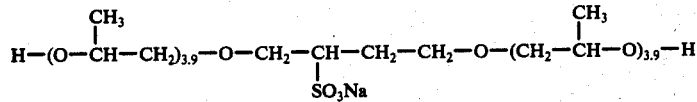

As in Example 5, sodium bisulphite was added to 540 g (1 mol) of propoxylated 1,4-dihydroxy-2-butene (total degree of propoxylation $2n = 7.8$) in aqueous medium in the presence of finely dispersed air at a pH-value kept constant at 7.0 to 7.1. On completion of sulphonation, the required sulphonate was isolated in a yield of 85% (548 g) by extraction with methylene chloride.

EXAMPLE 7

Ethoxylated butane diol sulphonate

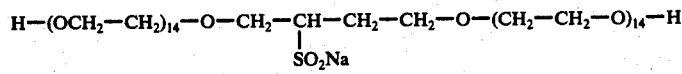

1320 g (1 mol) of ethoxylated 1,4-dihydroxy-2-butene (total degree of ethoxylation $n = 28$) were dissolved in 3 liters of water. 260 g (1 mol) of 40% sodium bisulphite solution, adjusted to pH 7.1 with dilute sodium hydroxide, were then added dropwise. At the same time, the required reaction was initiated by blowing in air through a glass frit.

The pH-value was kept at 7 to 7.1 by the addition of dilute $H_2SO_4$. The reaction was complete when there was no further change in the pH-value. The reaction mixture was acidified to pH- 2 with dilute $H_2SO_4$, followed by stirring for 1 hour in order to remove excess $SO_2$. After neutralization with dilute NaOH, the aqueous solution was concentrated to dryness and the residue extracted with 10 liters of methylene chloride. The required compound accumulated in an analytically pure form in a yield of 86% (1225 g).

What is claimed is:

1. Dihydroxy sulphonates containing ether groups and corresponding to the general formula $$H-(OCH-CH_2)_n-O-A-CH-B-O-(CH_2-CH-O)_nH$$
$$\phantom{H-(OC}|\phantom{H-CH_2)_n-O-A-C}|\phantom{H-B-O-(CH_2-C}|$$
$$\phantom{H-(OC}R\phantom{H-CH_2)_n-O-A-}SO_3X\phantom{H-B-O-(CH_2-C}R$$

in which,
A and B, which may be the same or different, represent straight-chain or branched alkylene radicals with 1 to 6 carbon atoms, the total number of carbon atoms in A and B being from 3 to 7,
R represents hydrogen $C_1$–$C_4$-alkyl or phenyl,
X represents $NH_4$ or an alkali metal, and
$n$ is a number from 1 to 30.

2. Dihydroxy sulphonates containing ether groups as claimed in claim 1 in which A in the general formula is a methylene group and B is —$CH_2$—$CH_2$—.

* * * * *